(12) United States Patent
Againe Csongor et al.

(10) Patent No.: US 7,737,142 B2
(45) Date of Patent: Jun. 15, 2010

(54) (THIO) CARBAMOYL-CYCLOHEXANE DERIVATIVES AS D3/D2 RECEPTOR ANTAGONISTS

(75) Inventors: Eva Againe Csongor, Budapest (HU); Janos Galambos, Budapest (HU); Katalin Nogradi, Budapest (HU); Istvan Vago, Budapest (HU); Istvan Gyertyan, Budapest (HU); Bela Kiss, Budapest (HU); Istvan Laszlovszky, Budapest (HU); Judit Laszy, Nagykovacsi (HU); Katalin Saghy, Budapest (HU)

(73) Assignee: Richter Gedeon Vegyeszeti Gyar Rt., Budapest (HU)

( * ) Notice: Subject to any disclaimer, the term of this patent is extended or adjusted under 35 U.S.C. 154(b) by 1040 days.

(21) Appl. No.: 11/337,275

(22) Filed: Jan. 20, 2006

(65) Prior Publication Data

US 2006/0229297 A1 Oct. 12, 2006

Related U.S. Application Data

(63) Continuation-in-part of application No. PCT/HU2004/000056, filed on May 21, 2004.

(30) Foreign Application Priority Data

Aug. 4, 2003 (HU) .................................. P0302451

(51) Int. Cl.
| | |
|---|---|
| A61P 25/00 | (2006.01) |
| A61K 31/535 | (2006.01) |
| A61K 31/497 | (2006.01) |
| A61K 31/4965 | (2006.01) |
| C07D 241/00 | (2006.01) |
| C07D 295/00 | (2006.01) |
| C07D 401/00 | (2006.01) |
| C07D 403/00 | (2006.01) |
| C07D 413/00 | (2006.01) |

(52) U.S. Cl. .............. 514/235.8; 514/252.11; 514/253.13; 514/254.01; 514/255.03; 544/121; 544/357; 544/360; 544/372; 544/393

(58) Field of Classification Search .............. 514/235.8, 514/252.11, 253.13, 254.01, 255.03; 544/121, 544/357, 360, 372, 393
See application file for complete search history.

(56) References Cited

U.S. PATENT DOCUMENTS

| 6,528,529 B1 | 3/2003 | Brann et al. |
| 2003/0144285 A1 | 7/2003 | Brann et al. |

FOREIGN PATENT DOCUMENTS

| WO | WO-97/11070 A1 | 3/1997 |
| WO | WO-99/50247 A1 | 10/1999 |
| WO | WO-99/67206 A1 | 12/1999 |
| WO | WO-01/05763 A2 | 1/2001 |
| WO | WO-03/029233 A1 | 4/2003 |

OTHER PUBLICATIONS

Glase et al.; "4-Bromo-1-Methoxy-N-[2-(4-Aryl-1-Piperazinyl)Ethyl]-2-Naphthalenecarboxamides: Selective Dopamine $D_3$ Receptor Partial Agonists"; Bioorganic & Medicinal Chemistry Letters, vol. 6, No. 12, pp. 1361-1366, Jun. 18, 1996.
International Search Report issued for International Application No. PCT/HU04/00056, date of mailing Nov. 11, 2004.
Belliotti et al., "Novel Cyclohexyl Amides as Potent and Selective $D_3$ Dopamine Receptor Ligands," Bioorg. Med. Chem. Lett. 1997, 7, 18, 2403-2408.
Levant, "The $D_3$ Dopamine Receptor: Neurobiology and Potential Clinical Relevance," Pharmacol. Rev. 1997, 49, 231-252.
Levant et al., "Dopamine $D_3$ Receptors: Relvance for the Drug Treatment of Parkinson's Disease," CNS Drugs 1999, 12, 391-402.
Levant et al., "$D_3$ dopamine receptors in rat spinal cord: implications for sensory and motor function," Neurosci. Lett. 2001, 303, 9-12.
Pilla et al., "Selective inhibition of cocaine-seeking behavior by a partial dopamine $D_3$ receptor agonist," Nature 1999, 400, 371-375.
Schwartz et al., "Dopamine $D_3$ Receptor: Basic and Clinical Aspects," Clin. Neuropharmacol. 1993, 16, 295-314.
Sokoloff et al., "Molecular cloning and characterization of a novel dopamine receptor ($D_3$) as a target for neuroleptics," Nature , 1990, 347, 146-151.
Wong et al., "Schizophrenia: from phenomenology to neurobiology," Neurosci. Biobehav. Rev. 2003, 27, 269-306.

*Primary Examiner*—Brenda L Coleman
(74) *Attorney, Agent, or Firm*—Fish & Richardson P.C.

(57) ABSTRACT

The present invention relates to new D3 and D2 dopamine receptor subtype preferring ligands of formula (I):

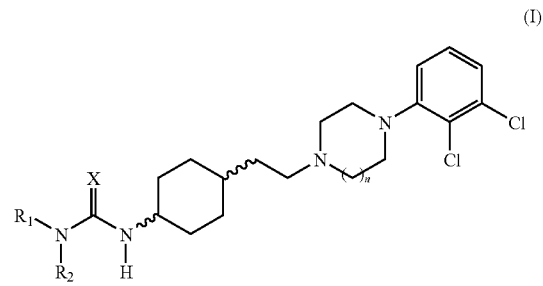

wherein $R_1$ and $R_2$ represent independently a substituent selected from hydrogen, alkyl, aryl, cycloalkyl, aroyl, or $R_1$ and $R_2$ may form a heterocyclic ring with the adjacent nitrogen atom; X represents an oxygen or sulphur atom; n is an integer of from 1 to 2, and/or geometric isomers and/or stereoisomers and/or diastereomers and/or salts and/or hydrates and/or solvates thereof, to the processes for producing the same, to pharmaceutical compositions containing the same and to their use in therapy and/or prevention of a condition which requires modulation of dopamine receptors.

28 Claims, No Drawings

(THIO) CARBAMOYL-CYCLOHEXANE DERIVATIVES AS D3/D2 RECEPTOR ANTAGONISTS

This application is a continuation-in-part of International Application No. PCT/HU2004/000056, filed May 21, 2004, which was published in English as International Publication No. WO 2005/012266 and claims the benefit of Hungarian Patent Application No. P0302451, filed Aug. 4, 2003, both of which are hereby incorporated by reference.

FIELD OF THE INVENTION

The present invention relates to new $D_3$ and $D_2$ dopamine receptor subtype preferring ligands of formula (I) and/or geometric isomers and/or stereoisomers and/or diastereomers and/or salts and/or hydrates and/or solvates thereof, to the processes for producing the same, to pharmacological compositions containing the same and to their use in therapy and/or prevention of a condition which requires modulation of dopamine receptors.

DESCRIPTION OF THE PRIOR ART

Cyclohexane derivatives are described in patent application WO 99/67206 useful in the therapy for the treatment of pain.

The compounds mentioned in the above publications are not declared or even not suggested having activity on the dopamine $D_3$ and/or $D_2$ receptors.

SUMMARY OF THE INVENTION

Surprisingly it was found that in contrast to the known above mentioned structurally analogous compounds the new derivatives of formula (I) of the present invention have high or very high affinity for dopamine $D_3$ receptors and moderate to high affinity to dopamine $D_2$ receptors always in such a combination that the $D_3$ affinity is 5 to 200 fold higher than the $D_2$ affinity. In addition, the compounds have even higher selectivity over other receptors, such as alpha-1 receptors. The dual (i.e. $D_3$ and $D_2$) receptor functional antagonism coupled in the above mentioned particular proportion is especially important as it allows the simultaneous manifestation of the beneficial effects of modulation of both the $D_3$ and $D_2$ receptors, however, without the appearance of the known disadvantages of each individual receptor action.

This type of new molecules belonging to the structure of formula (I) will be referred further on in this application as "$D_3/D_2$ ligands with $D_3$ preference".

The invention relates to new cyclohexane derivatives having (thio)carbamoyl side chain of formula (I):

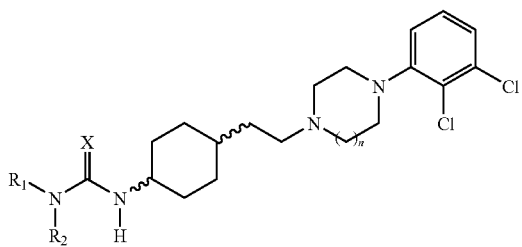

(I)

wherein $R_1$ and $R_2$ represent independently a substituent selected from hydrogen, alkyl, aryl, alkenyl, cycloalkyl, aroyl, or $R_1$ and $R_2$ may form a heterocyclic ring with the adjacent nitrogen atom;

X represents an oxygen or sulphur atom;

n is an integer of 1 to 2, and/or geometric isomers and/or stereoisomers and/or diastereomers and/or salts and/or hydrates and/or solvates thereof, to the processes for producing the same, to pharmacological compositions containing the same and to their use in therapy and/or prevention of pathological conditions which require the modulation of dopamine receptors such as psychoses (e.g. schizophrenia, schizo-affective disorders, etc.), drug (e.g. alcohol, cocaine and nicotine, opioids, etc.) abuse, cognitive impairment accompanying schizophrenia, mild-to-moderate cognitive deficits, dementia, psychotic states associated with dementia, eating disorders (e.g. bulimia nervosa, etc.), attention deficit disorders, hyperactivity disorders in children, psychotic depression, mania, paranoid and delusional disorders, dyskinetic disorders (e.g. Parkinson's disease, neuroleptic induced parkinsonism, tardive dyskinesias) anxiety, sexual dysfunction, sleep disorders, emesis, aggression, autism.

DETAILED DESCRIPTION OF THE INVENTION

The invention relates to new cyclohexane derivatives having (thio)carbamoyl side chain of formula (I):

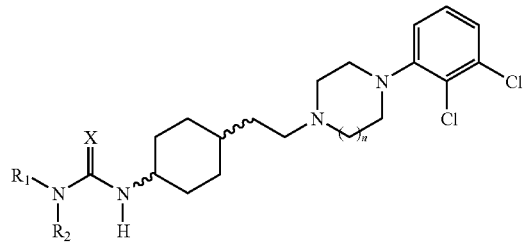

(I)

wherein $R_1$ and $R_2$ represent independently a substituent selected from hydrogen, alkyl, alkenyl, aryl, cycloalkyl, aroyl, or $R_1$ and $R_2$ may form a heterocyclic ring with the adjacent nitrogen atom;

X represents an oxygen or sulphur atom;

n is an integer of 1 to 2, and/or geometric isomers and/or stereoisomers and/or diastereomers and/or salts and/or hydrates and/or solvates thereof.

When $R_1$ and/or $R_2$ represent alkyl, the alkyl moiety may contain 1 to 6 carbon atoms with straight or branched chain optionally substituted with one or more $C_{1-6}$ alkoxycarbonyl, aryl, preferably phenyl or ($C_{1-6}$ alkoxycarbonyl)-$C_{1-6}$ alkyl group.

$R_1$ and $R_2$ may form a heterocyclic ring with the adjacent nitrogen atom, which may be saturated or unsaturated optionally substituted monocyclic or bicyclic ring, which may contain further heteroatoms selected from O, N, or S. The heterocyclic ring is preferably pyrrolidine, piperazine, piperidine or morpholine ring.

When $R_1$ and/or $R_2$ represent alkenyl, the alkenyl moiety may have 2 to 7 carbon atoms and 1 to 3 double bonds.

When $R_1$ and/or $R_2$ represent aryl, the aryl moiety may be selected from an optionally substituted mono-, bi- or tricyclic aryl, such as phenyl, naphthyl, fluorenonyl, or antraquinonyl group, preferably phenyl or naphthyl. The aryl moiety may be substituted with one or more $C_{1-6}$ alkoxy, trifluoro-$C_{1-6}$ alkoxy, $C_{1-6}$ alkoxycarbonyl, $C_{1-6}$ alkanoyl, aryl, $C_{1-6}$ alkylthio, halogen or cyano. The aryl is as defined above.

When $R_1$ and/or $R_2$ represent cycloalkyl, the cycloalkyl moiety may be selected from an optionally substituted mono-, bi- or tricyclic cycloalkyl group, such as cyclohexyl or adamantyl.

When $R_1$ and/or $R_2$ represent aroyl the aryl moiety therein is as defined above, preferably phenyl.

The invention relates also to the salts of compounds of formula (I) formed with acids.

Both organic and inorganic acids can be used for the formation of acid addition salts. Suitable inorganic acids can be for example hydrochloric acid, sulfuric acid, nitric acid and phosphoric acid. Representatives of monovalent organic acids can be for example formic acid, acetic acid, propionic acid, and different butyric acids, valeric acids and capric acids. Representatives of bivalent organic acids can be for example oxalic acid, malonic acid, maleic acid, fumaric acid and succinic acid. Other organic acids can also be used, such as hydroxy acids for example citric acid, tartaric acid, or aromatic carboxylic acids for example benzoic acid or salicylic acid, as well as aliphatic and aromatic sulfonic acids for example methanesulfonic acid, naphtalenesulfonic acid and p-toluenesulfonic acid. Especially valuable group of the acid addition salts is in which the acid component itself is physiologically acceptable and does not have therapeutical effect in the applied dose or it does not have unfavourable influence on the effect of the active ingredient. These acid addition salts are pharmaceutically acceptable acid addition salts. The reason why acid addition salts, which do not belong to the pharmaceutically acceptable acid addition salts belong to the present invention is, that in given case they can be advantageous in the purification and isolation of the desired compounds.

Solvates and/or hydrates of compounds of formula (I) are also included within the scope of the invention.

The compounds of formula (I) exist in the form of cis and trans isomers with respect to the configuration of the cyclohexane ring. These and their mixtures are likewise within the scope of the present invention. The compounds of the invention are preferably in trans configuration.

Certain compounds of formula (I) when the compound contains $C_{2-7}$ alkenyl group can exist in the form of cis- and/or trans-isomers. These are likewise within the scope of the present invention including all such isomers and the mixtures thereof.

Certain compounds of formula (I) can exist as stereoisomers and diastereomers, too. These and the mixtures thereof are likewise within the scope of the present invention.

As the invention relates also to the salts of compounds of formula (I) formed with acids, especially the salts formed with pharmaceutically acceptable acids, the meaning of compound of formula (I) is either the free base or the salt even if it is not referred separately.

Preferred compounds of the invention are those compounds of formula (I), wherein $R_1$ and $R_2$ represent independently hydrogen, or $C_{1-6}$ alkyl, with straight or branched chain optionally substituted with one or more $C_{1-6}$ alkoxycarbonyl, aryl, or ($C_{1-6}$ alkoxycarbonyl)-$C_{1-6}$ alkyl group, or $R_1$ and $R_2$ may form a heterocyclic ring with the adjacent nitrogen atom, which may be saturated or unsaturated optionally substituted monocyclic or bicyclic ring, which may contain further heteroatoms selected from O, N, or S, or $C_{2-7}$ alkenyl with 1 to 3 double bond, or a mono-, bi- or tricyclic aryl optionally substituted with one or more $C_{1-6}$ alkoxy, trifluoro $C_{1-6}$ alkoxy, $C_{1-6}$ alkoxycarbonyl, $C_{1-6}$ alkanoyl, aryl, $C_{1-6}$ alkylthio, halogen or cyano, or an optionally substituted mono-, bi- or tricyclic cycloalkyl group, or aroyl group;

X represents oxygen or sulphur atom;

n is an integer of 1 to 2, and/or geometric isomers and/or stereoisomers and/or diastereomers and/or salts and/or hydrates and/or solvates thereof.

Particularly preferred compounds of the invention are those compounds of formula (I), wherein $R_1$ and $R_2$ represent independently hydrogen, or $C_{1-6}$ alkyl, with straight or branched chain and optionally substituted with one or more $C_{1-6}$ alkoxycarbonyl, phenyl or ($C_{1-6}$ alkoxycarbonyl)-$C_{1-6}$ alkyl group or $R_1$ and $R_2$ may form a heterocyclic ring with the adjacent nitrogen atom, which may be saturated optionally by $C_{1-6}$ alkyl or hydroxy substituted monocyclic ring, which may contain further heteroatoms selected from O or N, or $C_{2-7}$ alkenyl with 1 double bond, or phenyl or naphthyl group optionally substituted with one or more $C_{1-6}$ alkoxy, trifluoro-$C_{1-6}$ alkoxy, $C_{1-6}$ alkoxycarbonyl, $C_{1-6}$ alkanoyl, aryl, $C_{1-6}$ alkylthio, halogen or cyano, or cyclohexyl or adamantyl group, or benzoyl group;

X represents oxygen or sulphur atom;

n is an integer of 1 to 2, and/or geometric isomers and/or stereoisomers and/or diastereomers and/or salts and/or hydrates and/or solvates thereof.

The most prominent compounds of the invention are those compounds of formula (I), wherein $R_1$ and $R_2$ represent independently hydrogen, or $C_{1-6}$ alkyl with straight or branched chain optionally substituted with $C_{1-6}$ alkoxycarbonyl, or phenyl or $R_1$ and $R_2$ form with the adjacent nitrogen atom an optionally by $C_{1-6}$ alkyl or hydroxy substituted pyrrolidine, piperazine, piperidine or morpholine ring;

allyl;

phenyl optionally substituted with one or more $C_{1-6}$ alkoxy, cyano or $C_{1-6}$ alkanoyl;

cyclohexyl;

X represents oxygen or sulphur;

n is 1, and/or geometric isomers and/or stereoisomers and/or diastereomers and/or salts and/or hydrates and/or solvates thereof.

The invention also relates to the pharmaceutical compositions containing the compounds of formula (I) as active ingredient.

Further subject of the present invention is the pharmaceutical manufacture of medicaments containing compounds of formula (I), as well as the process of treatments and/or prevention with these compounds, which means administering to a mammal to be treated—including human—effective amount/amounts of compounds of formula (I) of the present invention as such or as medicament.

The present invention also provides a process (Method A) for preparing compounds of formula (I) by forming an amide bond between a (thio)carbamoylchoride of formula (II):

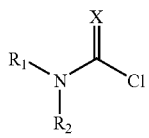
(II)

wherein $R_1$, $R_2$ and X is as described above for the formula (I);

and an amine of formula (III):

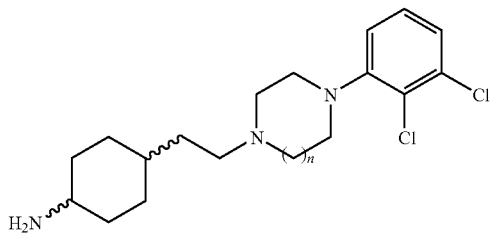
(III)

wherein the meaning of n is as described above for the formula (I), or derivatives thereof.

The amide bond formation may be carried out by known methods, preferably by suspending or dissolving the appropriate amine (III) or a salt thereof in a suitable solvent (e.g. tetrahydrofurane, dimethylformamide or chlorinated hydrocarbons or hydrocarbons) and reacting it with the appropriate (thio)carbamoylchloride (II) in the presence of a base (e.g. triethylamine). The reaction can be carried out advantageously between −10° C. and 60° C. The reactions are followed by thin layer chromatography. The necessary reaction time is about 6-60 h. The work-up of the reaction mixture can be carried out by known methods. The products can be purified, e.g. by crystallization or by column chromatography.

Another process (Method B) for preparing the compounds of formula (I) by forming an amide bond between the iso(thio)cyanate of formula (IV):

(IV)

wherein the meaning of $R_1$ and X is as described above for the formula (I), and an amine of formula (III):

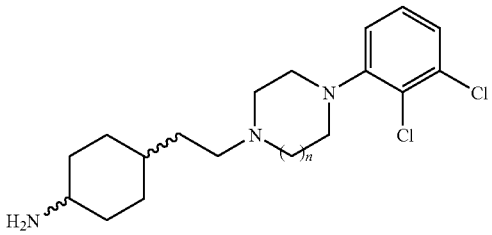
(III)

wherein the meaning of n is as described above for the formula (I), or derivatives thereof.

The amide bond formation may be carried out by known methods, preferably by suspending or dissolving the appropriate amine (III) or a salt thereof in a suitable solvent (e.g. tetrahydrofurane, dimethylformamide or chlorinated hydrocarbons or hydrocarbons) and reacting it with the appropriate iso(thio)cyanates (IV) if necessary in the presence of a base (e.g. triethylamine). The reaction can be carried out advantageously between 5° C. and 50° C. The reactions are followed by thin layer chromatography. The necessary reaction time is about 6-10 h. The work-up of the reaction mixture can be carried out by known methods. The products can be purified, e.g. by crystallization or by column chromatography.

Method B may be carried out also by using automated parallel synthesis.

Another process (Method C) for preparing compounds of formula (I) is transforming in situ an amine of formula (III) to iso(thio)cyanate derivative and reacting the latter with an amine of formula (V):

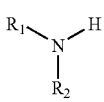
(V)

wherein $R_1$ and $R_2$ are as described above for the formula (I), or derivatives thereof.

The above reaction may be carried out by known methods. The transformation of amine (III) to iso(thio)cyanate derivative may be carried out in situ in an aprotic solvent (e.g. tetrahydrofurane, chlorinated hydrocarbons) by the use of an appropriate (thio)carbonic acid derivative (e.g. phosgene, triphosgene, thiophosgene) in the presence of a base (e.g. triethylamine), advantageously between −5° C. and room temperature. To the thus obtained solution or suspension an appropriate amine of formula (V), wherein $R_1$ and $R_2$ are as described above, is added in the form of base or salt formed with organic or inorganic acid. The necessary reaction time is between 2-24 hours. The work-up of the reaction mixture can be carried out by known methods. The products can be purified, e.g. by crystallization or by column chromatography.

The obtained (thio)ureas of formula (I) can be transformed into the salts thereof with acids and/or liberated the (thio)ureas of formula (I) from the obtained acid addition salts by treatment with a base, and/or the cis- and/or trans-isomers and/or the stereoisomers and/or diastereomers can be separated and/or can be transformed into hydrates and/or solvates thereof.

The (thio)carbamoylchlorides of formula (II) and iso(thio)cyanates of formula (IV) and the amines of formula (V), wherein $R_1$, $R_2$ and X are as defined above, are either commercially available or can be synthesized by different known methods.

The synthesis of amine of formula (III), wherein n=1 is described e.g. in WO 03/029233 or in Bioorg. Med. Chem. Lett.; EN; 7; 18; 1997; 2403-2408.

The amines of formula (III), wherein n=2, are new compounds and are also included within the scope of the present invention.

The new amines of formula (III), wherein n=2 are synthesized by conventional known methods mentioned above.

The compounds of formula (I) can also be prepared by automated parallel synthesis.

The separation of cis- and trans isomers either of compounds of formula (I) or of formula (III) or the protected derivatives of the latter is carried out by conventional methods, e.g. by chromatography and/or crystallization, or the cis and trans isomers of formula (I) can be prepared from the pure cis or trans precursor.

The compounds of formula (I) of the present invention, in contrast to known antipsychotics, have been found to exhibit high affinity for dopamine $D_3$ receptors, less activity toward $D_2$ receptors and much less affinity to aderenergic alpha-1 receptors, and are expected to be useful in the treatment of disease states and/or prevention the same in which dopamine $D_3$ and/or $D_2$ receptors are involved in the disease pathology and thus their modulation is required.

Dysfunction of the dopaminergic neurotransmitter system is involved in the pathology of several neuropsychiatric and neurodegenerative disorders, such as schizophrenia, drug abuse and Parkinson's disease, respectively. The effect of dopamine is mediated via at least five distinct dopamine receptors belonging to the $D_1$-($D_1$, $D_5$) or the $D_2$-($D_2$, $D_3$, $D_4$) families. $D_3$ receptors have been shown to have characteristic distribution in the cerebral dopaminergic systems. Namely, high densities were found in certain limbic structures, such as nucleus accumbens and islands of Calleja. Therefore, preferential targeting of the $D_3$ receptors may be a promising approach for more selective modulation of dopaminergic functions and consequently for successful therapeutic intervention in several abnormalities, such as schizophrenia, emotional or cognitive dysfunctions and addiction (Sokoloff, P. et al.: Nature, 1990, 347, 146; Schwartz, J. C., et al.: Clin. Neuropharmacol. 1993, 16, 295; Levant, B.: Pharmacol. Rev. 1997, 49, 231), addiction (Pilla, C. et al.: Nature 1999, 400, 371) and Parkinson's disease (Levant, B. et al.: CNS Drugs 1999, 12, 391) or pain (Levant, B. et al.: Neurosci. Lett. 2001, 303, 9).

The dopamine $D_2$ receptors are widely distributed in the brain and are known to be involved in numerous physiological functions and pathological states. $D_2$ antagonists are widely used drugs as antipsychotics, for example. However, it is also well known that massive antagonism of the $D_2$ receptors leads to unwanted side-effects such as extrapyramidal motor symptoms, psychomotor sedation or cognitive disturbances. These side effects seriously restrict the therapeutic utilization of $D_2$ antagonist compounds. (Wong A. H. C. et al.: Neurosci. Biobehav. Rev. 2003, 27, 269.).

The present invention provides novel compounds of formula (I) and/or geometric isomers and/or stereoisomers and/or diastereomers and/or salts and/or hydrates and/or solvates thereof which have high (less than 10 nM) or very high (less than 1 nM) affinity to dopamine $D_3$ receptors and—simultaneously—have moderate (between 50 and 200 nM) to high (between 1 and 10 nM) affinity to $D_2$ receptors always in such combination that the $D_3$ affinity is 5 to 200 fold higher than the $D_2$ affinity.

In a further aspect of the present invention it provides a method of treating conditions which require preferential modulation of dopamine $D_3$ and/or $D_2$ receptors, for example psychoses (e.g. schizophrenia, schizo-affective disorders), cognitive impairment accompanying schizophrenia, mild-to-moderate cognitive deficits, dementia, psychotic states associated with dementia, psychotic depression, mania, paranoid and delusional disorders, dyskinetic disorders such as Parkinson's disease, neuroleptic induced parkinsonism, tardive dyskinesia, eating disorders (e.g. bulimia nervosa), attention deficit disorders, hyperactivity disorders in children, depression, anxiety, sexual dysfunction, sleep disorders, emesis, aggression, autism and drug abuse, which comprises administering to a subject in need thereof an effective amount of a compound of formula (I) and/or geometric isomers and/or stereoisomers and/or diastereomers and/or salts and/or hydrates and/or solvates thereof.

The invention also provides the use of a compound of formula (I) and/or geometric isomers and/or stereoisomers and/or diastereomers and/or salts and/or hydrates and/or solvates thereof in the manufacture of a medicament for the treatment of conditions which require modulation of dopamine receptors especially that of dopamine $D_3$ and/or $D_2$ receptors.

A preferred use for $D_3/D_2$ antagonists with $D_3$ preference according to the present invention is in the treatment of schizophrenia, schizo-affective disorders, cognitive impairment accompanying schizophrenia, mild-to-moderate cognitive deficits, dementia, psychotic states associated with dementia, psychotic depression, mania, paranoid and delusional disorders, dyskinetic disorders such as Parkinson's disease, neuroleptic induced parkinsonism, depression, anxiety, drug abuse (e.g. cocaine abuse).

The particular combination of the two receptor-actions described above allows the simultaneous manifestation of the beneficial actions of both the $D_3$ antagonism (e.g. cognitive enhancer effect, inhibition of extrapyramidal motor symptoms, inhibitory action on drug abuse) and the $D_2$ antagonism (e.g. antipsychotic effect). Furthermore, the same combination surprisingly results in cancelling out the disadvantageous features of $D_2$ antagonism (e.g. extrapyramidal symptoms, psychomotor sedation, cognitive disturbances).

For use in medicine, the compounds of formula (I) of the present invention and/or geometric isomers and/or stereoisomers and/or diastereomers and/or physiologically acceptable salts and/or hydrates and/or solvates thereof are usually administered as a standard pharmaceutical composition. The present invention therefore provides in a further aspect pharmaceutical compositions comprising a new compound of formula (I) and/or geometric isomers and/or stereoisomers and/or diastereomers and/or physiologically acceptable salts and/or hydrates and/or solvates thereof and physiologically acceptable carriers.

The compounds of formula (I) of the present invention and/or geometric isomers and/or stereoisomers and/or diastereomers and/or physiologically acceptable salts and/or hydrates and/or solvates thereof may be administered by any convenient method, for example by oral, parental, buccal, sublingual, nasal, rectal or transdermal administration and the pharmaceutical compositions adapted accordingly.

The compounds of formula (I) of the present invention and/or geometric isomers and/or stereoisomers and/or diastereomers and/or physiologically acceptable salts and/or hydrates and/or solvates thereof which are active when given orally can be formulated as liquids or solids, for example syrups, suspensions or emulsions, tablets, capsules and lozenges.

A liquid formulation of the compounds of formula (I) of the present invention and/or geometric isomers and/or stereoisomers and/or diastereomers and/or physiologically acceptable salts and/or hydrates and/or solvates thereof generally consists of a suspension or solution of the compound of formula (I) and/or geometric isomers and/or stereoisomers and/or diastereomers and/or salts and/or hydrates and/or solvates thereof in a suitable liquid carrier(s) for example an aqueous solvent, such as water, ethanol or glycerine, or a non-aqueous solvent, such as polyethylene glycol or an oil. The formulation may also contain a suspending agent, preservative, flavouring or colouring agent.

A composition in the solid form of a tablet can be prepared using any suitable pharmaceutical carrier(s) routinely used for preparing solid formulations. Examples of such carriers include magnesium stearate, starch, lactose, sucrose, cellulose etc.

A composition in the solid form of a capsule can be prepared using routine encapsulation procedures. For example, pellets containing the active ingredient can be prepared using standard carriers and then filled into a hard gelatine capsule; alternatively, a dispersion or suspension can be prepared using any suitable pharmaceutical carrier(s), for example aqueous gums, celluloses, silicates or oils and the dispersion or suspension then filled into a soft gelatine capsule.

Typical parenteral compositions consist of a solution or suspension of the compound of formula (I) of the present invention and/or geometric isomers and/or stereoisomers and/or diastereomers and/or physiologically acceptable salts and/or hydrates and/or solvates thereof in a steril aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions of the present invention for nasal administration containing a compound of formula (I) and/or geometric isomers and/or stereoisomers and/or diastereomers and/or physiologically acceptable salts and/or hydrates and/or solvates thereof may conveniently be formulated as aerosols, drops, gels and powders. Aerosol formulations of the present invention typically comprise a solution or fine suspension of the compound of formula (I) and/or geometric isomers and/or stereoisomers and/or diastereomers and/or physiologically acceptable salts and/or hydrates and/or solvates thereof in a physiologically acceptable aqueous or non-aqueous solvent and are usually presented in a single or multidose quantities in steril form is a sealed container, which can take the form of a cartridge or refill for use with an atomising device. Alternatively, the sealed container may be a unitary dispensing device, such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas, such as compressed air or an organic propellant, such as a fluorochlorohydrocarbon. The aerosol dosages form can also take the form of a pump-atomiser. Compositions of the present invention containing a compound of formula (I) and/or geometric isomers and/or stereoisomers and/or diastereomers and/or physiologically acceptable salts and/or hydrates and/or solvates thereof suitable for buccal or sublingual administration include tablets, lozenges and pastilles, wherein the active ingredient is formulated with a carrier, such as sugar and acacia, tragacanth, or gelatine and glycerin etc.

Compositions of the present invention containing a compound of formula (I) and/or geometric isomers and/or stereoisomers and/or diastereomers and/or physiologically acceptable salts and/or hydrates and/or solvates thereof for rectal administration are conveniently in the form of suppositories containing a conventional suppository base, such as cocoa butter.

Compositions of the present invention containing a compound of formula (I) and/or geometric isomers and/or stereoisomers and/or diastereomers and/or physiologically acceptable salts and/or hydrates and/or solvates thereof for transdermal administration include ointments, gels and patches.

The compositions of the present invention containing a compound of formula (I) and/or geometric isomers and/or stereoisomers and/or diastereomers and/or physiologically acceptable salts and/or hydrates and/or solvates thereof are preferably in the unit dose form, such as tablet, capsule or ampoule.

Each dosage unit of the present invention for oral administration contains preferably from 1 to 250 mg of a compound of formula (I) and/or geometric isomers and/or stereoisomers and/or diastereomers and/or physiologically acceptable salts and/or hydrates and/or solvates thereof calculated as a free base.

Each dosage unit of the present invention for parenteral administration contains preferably from 0.1 to 2 mg of a compound of formula (I) and/or geometric isomers and/or stereoisomers and/or diastereomers and/or physiologically acceptable salts and/or hydrates and/or solvates thereof calculated as a free base.

The physiologically acceptable compounds formula (I) of the present invention and/or geometric isomers and/or stereoisomers and/or diastereomers and/or physiologically acceptable salts and/or hydrates and/or solvates thereof can normally be administered in a daily dosage regimen (for an adult patient) of, for example, an oral dose between 1 mg and 500 mg, preferably between 10 mg and 400 mg, e.g. between 10 mg and 250 mg or an intravenous, subcutaneous, or intramuscular dose of between 0.1 mg and 100 mg, preferably between 0.1 mg and 50 mg, e.g. between 1 and 25 mg of the compound of formula (I) and/or geometric isomers and/or stereoisomers and/or diastereomers and/or physiologically acceptable salts and/or hydrates and/or solvates thereof calculated as the free base. The compounds of the present invention can be administered 1 to 4 times per day. The compounds of the present invention can suitably be administered for a period of continuos therapy, for example for a week or more.

Biological Test Methods

Receptor Binding Assays

1. $D_3$ Receptor Binding

Binding assays were carried out on rat recombinant $D_3$ receptors (expressed in Sf9 cells) according to the supplier instruction (Packard BioScience, BioSignal Packard Inc. Cat. No. 6110139, Technical Data Sheet) using [$^3$H]-spiperone (0.85 nM) as ligand and haloperidol (10 μM) for determination of non-specific binding.

2. $D_2$ Receptor Binding $D_2$ receptor binding assay was carried out as described by Creese et al. (European Journal of Pharmacology 60:55-66, 1979) on rat brain striatal membrane preparation using [$^3$H]- spiperone (0.6 nM) as ligand. The non-specific binding was determined in the presence of 1 μM (+)-butaclamol.

3. Alpha-1 Receptor Binding

Alpha-1 receptor binding study was performed according to the method described by Greengrass and Bremmer (European Journal of Pharmacology 55:323-326, 1979) on rat brain cortical membrane preparation using [$^3$H]-prasosin (0.5 nM) as ligand. The non-specific binding was determined in the presence of 10 μM phentolamine.

$D_3$ and $D_2$ and alpha-1 receptor binding data of selected compounds of the invention are listed in the Table hereinbelow.

| Compound | D3 IC-50 (nM) | D2 IC-50 (nM) | Alfa-1 IC-50 (nM) |
|---|---|---|---|
| 1 | +++ | ++ | >200 |
| 2 | ++++ | ++ | >200 |
| 4 | ++++ | ++ | >200 |
| 5 | ++++ | ++ | >200 |
| 6 | ++++ | ++ | >200 |
| 7 | +++ | ++ | >200 |
| 8 | ++++ | ++ | >200 |
| 9 | ++++ | +++ | >200 |
| 16 | ++++ | ++ | >200 |
| 21 | ++++ | ++ | >200 |
| 24 | ++++ | ++ | >200 |
| 29 | +++ | ++ | >200 |
| 31 | ++++ | ++ | >200 |
| 32 | ++++ | ++ | >200 |
| 33 | ++++ | ++ | >200 |
| 38 | +++ | ++ | >200 |
| 42 | ++++ | ++ | >200 |
| 44 | ++++ | ++ | >200 |
| 45 | ++++ | ++ | >200 |
| 47 | ++++ | ++ | >200 |
| 48 | ++++ | ++ | >200 |
| 49 | ++++ | + | >200 |
| 50 | ++++ | + | >200 |
| 51 | ++++ | ++ | >200 |
| Haloperidol | + | ++ | ++ |
| Aripiprazole | +++ | ++ | >200 |
| Risperidone | ++ | ++ | +++ |
| Olanzapine | + | + | ++ |

+: IC-50 is between 50 and 200 nM
++: IC-50 is between 10 and 50 nM
+++: IC-50 is between 1 and 10 nM
++++: IC-50 is less than 1 nM
>200: IC-50 value is higher than 200 nM The most prominent side effects of the first generation antipsychotic compounds (e.g. chlorpromazine and haloperidol) are the extrapyramidal symptoms such as pseudoparkinsonism and tardive dyskinesia and the orthostatic hypotension. The former two are the result of massive blockade of $D_2$ receptors in the basal ganglia whereas the latter is the consequence of antagonism of alpha-1 receptors.

Compounds in the above Table are highly or very highly potent ligands at $D_3$ receptors (IC-50 values are less than 1 nM or between 1 and 10 nM, respectively) and moderately to highly potent ligands at dopamine $D_2$ receptors showing 5 to 200 fold selectivity (selectivity: IC-50 for $D_2$ divided by IC-50 for $D_3$) over $D_2$ receptors. However, coupling the high or very high $D_3$ affinity to the moderate to high $D_2$ affinity in this particular proportion allows to preserve the beneficial (e.g. antipsychotic) actions of a $D_2$ antagonist while—at the same time—impedes (by the $D_3$ antagonism) the appearance of the disadvantageous consequences of massive $D_2$ receptor blockade like extrapyramidal symptoms or cognitive disturbances. It is therefore anticipated that no or greatly diminished adverse effects related to $D_2$ receptors will occur in the course of therapeutical application of compounds of the present invention. In addition, the compounds have very low or practically no affinity to adrenergic alpha-1 receptors (IC-50 higher than 200 nM for each compound) and thus have extremely high $D_3$/alpha-1 selectivity (ranging from several hundred-fold to several thousand fold). From the very low or no affinity of the compounds to adrenergic alpha-1 receptors the lack of cardiovascular side effects (e.g. orthostatic hypotension) is anticipated.

The invention is further illustrated by the following non-limiting examples.

The structure of all intermediates and end products were elucidated by IR, NMR and MS spectroscopy.

Example 1

1-(2,3-dichlorophenyl)-[1,4]diazepine (starting material)

2.25 g (10 mmol) 1-bromo-2,3-dichloro-benzene was dissolved in dry toluene (50 ml), 2.3 (11 mmol) of [1,4]diazepine-1-carboxylic acid tert-butylester was added followed by 0.2 g BINAP (2,2-bis(diphenylphosphino)-1,1'-binaphtyl), 85 mg tris(dibenzylideneacetone)dipalladium(0) and 1.2 g (12 mmol) sodium-tert-butoxyde. The reaction mixture was refluxed for eight hours and filtered. The organic layer was washed with water, dried and evaporated in vacuo. The residue was purified by chromatography and deprotected at 10° C. using 20 ml ethylacetate saturated with gaseous hydrochloric acid, the precipitate was filtered giving 2.1 g (yield: 75%) hydrochloride salt of the title compound, melting at 182-3° C.

Example 2

Trans-N-{4-[2-[4-(2,3-dichloro-phenyl)-hexahydro-[1,4]diazepin-1-yl]-ethyl]-cyclohexyl}-carbamic acid tert-butylester (intermediate)

0.7 g (2.5 mmol) of 1-(2,3-dichlorophenyl)-[1,4]diazepine hydrochloride and 0.6 g (2.5 mmol) of trans-2-{1-[4-(N-tert-butyloxycarbonyl)amino]cyclohexyl}-acetaldehyde were dissolved in dichloroethane (35 ml), 0.35 ml (2.5 mmol) triethylamine was added, then 0.79 g (3.7 mmol) sodium triacetoxyborohydride was added portionswise and the reaction mixture was stirred for 20 hours at ambient temperature, then 20% potassium carbonate solution in water (20 ml) was added. The organic layer was separated, dried and evaporated to dryness in vacuo. The precipitate was recrystallized from acetonitrile to give the title compound 1.0 g (yield: 85.8%), m.p.: 95-8° C.

Example 3

Trans-4-[2-[4-(2,3-dichloro-phenyl)-hexahydro-[1,4]diazepin-1-yl]-ethyl]-cyclohexylamine (intermediate)

0.93 g (2.1 mmol) trans-N-{4-[2-[4-(2,3-dichloro-phenyl)-hexahydro-[1,4]diazepin-1-yl]-ethyl]-cyclohexyl}-carbamic acid tert-butylester was deprotected at 10° C. using 15 ml ethylacetate saturated with gaseous hydrochloric acid, after 4 hours the precipitate was filtered giving 0.91 g (yield: 98%) dihydrochloride salt of the title compound, melting at 260-6° C.

Method A

Trans-1-{4-[2-[4-(2,3-dichlorophenyl)-piperazin-1-yl]-ethyl]-cyclohexyl}-3,3-dimethyl-urea (compound 1)

1.39 g (3 mmol) trans-4-{2-[4-(2,3-dichlorophenyl)-piperazin-1-yl]-ethyl}-cyclohexyl-amine trihydrochloride was suspended in dichloromethane (100 ml), triethylamine (2.1 ml, 15 mmol) was added followed by 0.30 ml (3.3 mmol) N,N-dimethylcarbamoylchloride. The reaction mixture was stirred for 48 hours at room temperature, filtered. The filtrate was washed with water (2×20 ml), dried and evaporated in vacuo. Recrystallizing from methanol gave the title compound (0.83 g, 65%), melting at 212-4° C.

Method B

Trans-1-{4-[2-[4-(2,3-dichlorophenyl)-piperazin-1-yl]-ethyl]-cyclohexyl}-3-ethyl-urea (compound 2)

0.56 g (1.2 mmol) trans-4-{2-[4-(2,3-dichlorophenyl)-piperazin-1-yl]-ethyl}-cyclohexyl-amine was dissolved in dry dichloromethane (20 ml), ethylisocyanate (0.1 ml, 1.3 mmol) was added and the reaction mixture was stirred at room temperature for 4 hours. The solvent was removed in vacuo. The residue was stirred with water, the precipitate was filtered, giving the title compound (0.33 g, 65%). Melting point: 235-8° C.

Method C

Trans-1-{4-[2-[4-(2,3-dichlorophenyl)-piperazin-1-yl]-ethyl]-cyclohexyl}-3,3-dimethyl-urea (compound 1)

0.56 g (1.2 mmol) trans-4-{2-[4-(2,3-dichlorophenyl)-piperazin-1-yl]-ethyl}-cyclohexyl-amine trihydrochloride was suspended in dry dichloromethane (50 ml), triethylamine 0.77 ml, 6 mmol) was added and 0.13 g (0.44 mmol) triphosgene dissolved in dichloromethane was dropped in. After one hour stirring at room temperature dimetilamine hydrochloride (0.49 g, 6 mmol) followed by triethylamine (0.84 ml, 6 mmol) was added and the stirring was continued for 20 hours. The mixture was filtered, the filtrate washed with water, dried and evaporated in vacuo. Recrystallizing the product from methanol gave the title compound (0.27 g, 52%). Melting point: 212-4° C.

Applying one of the above procedures the following compounds were prepared:

trans-1-{4-[2-[4-(2,3-dichlorophenyl)-piperazin-1-yl]-ethyl]-cyclohexyl}-3-methyl-urea (compound 3), melting point: 210-4° C.;

trans-1-{4-[2-[4-(2,3-dichlorophenyl)-piperazin-1-yl]-ethyl]-cyclohexyl}-3-propyl-urea (compound 4), melting point: 218-20° C.;

trans-1-{4-[2-[4-(2,3-dichlorophenyl)-piperazin-1-yl]-ethyl]-cyclohexyl}-3-isopropyl-urea (compound 5), melting point: 227-30° C.;

trans-1-{4-[2-[4-(2,3-dichlorophenyl)-hexahydro[1,4]diazepin-1-yl]-ethyl]-cyclohexyl}-3-ethyl-urea (compound 6), melting point: 115-8° C.;

trans-1-{4-[2-[4-(2,3-dichlorophenyl)-hexahydro[1,4]diazepin-1-yl]-ethyl]-cyclohexyl}-3,3-dimethyl-urea (compound 7), melting point: 168-72° C.;

trans-N-{4-[2-[4-(2,3-dichlorophenyl)-piperazin-1-yl]-ethyl]-cyclohexyl}-pyrrolidine-1-carboxamide (compound 8), melting point: 201-3° C.;

trans-N-{4-[2-[4-(2,3-dichlorophenyl)-hexahydro[1,4]diazepin-1-yl]-ethyl]-cyclohexyl}-pyrrolidine-1-carboxamide (compound 9);

trans-1-{4-[2-[4-(2,3-dichlorophenyl)-piperazin-1-yl]-ethyl]-cyclohexyl}-3,3-diethyl-urea (compound 10), melting point: 171-3° C.;

trans-1-{4-[2-[4-(2,3-dichlorophenyl)-piperazin-1-yl]-ethyl]-cyclohexyl}-3-ethyl-3-methyl-urea (compound 11), melting point: 195-8° C.;

trans-1-{4-[2-[4-(2,3-dichlorophenyl)-piperazin-1-yl]-ethyl]-cyclohexyl}-3-methyl-3-propyl-urea (compound 12), melting point: 137-9° C.;

trans-1-{4-[2-[4-(2,3-dichlorophenyl)-piperazin-1-yl]-ethyl]-cyclohexyl}-urea (compound 13), melting point: 215-7° C.;

trans-N-{4-[2-[4-(2,3-dichlorophenyl)-piperazin-1-yl]-ethyl]-cyclohexyl}-piperazine-1-carboxamide (compound 14), melting point: 293-6° C.;

trans-N-{4-[2-[4-(2,3-dichlorophenyl)-piperazin-1-yl]-ethyl]-cyclohexyl}-4-methyl-piperazine-1-carboxamide (compound 15), melting point: 166-8° C.;

trans-N-{4-[2-[4-(2,3-dichlorophenyl)-piperazin-1-yl]-ethyl]-cyclohexyl}-morpholine-4-carboxamide (compound 16), melting point: 201-3° C.;

trans-N-{4-[2-[4-(2,3-dichlorophenyl)-piperazin-1-yl]-ethyl]-cyclohexyl}-piperidine-1-carboxamide (compound 17), melting point: 188-90° C.;

trans-N-{4-[2-[4-(2,3-dichlorophenyl)-piperazin-1-yl]-ethyl]-cyclohexyl}-4-hydroxy-piperidine-1-carboxam-ide (compound 18), melting point: 178-80° C.

Automated Parallel Synthesis (General Procedure)

0.1 mmol of trans-4-{2-[4-(2,3-dichloro-phenyl)-piperazin-1-yl]-ethyl}-cyclohexylamine was dissolved in 1 ml of dichloromethane, and 0.1 mmol of the appropriate isocyanate or isothiocyanate compound was added. The mixture was vigorously shaken for 12 hours. The solvent was evaporated in vacuo. 1 ml of n-hexane was added to the remaining solid and the mixture was vigorously shaken for 20 minutes. The solvent was decanted from the solid residue, and the solid was dried in vacuo.

Applying the above procedures the following compounds were prepared:

| compound | mol weight | k' | Purity (HPLC Area %) | Iupac |
|---|---|---|---|---|
| 19 | 505.49 | 5.768 | 99.4 | trans-1-(4-{2-[4-(2,3-Dichloro-phenyl)-piperazin-1-yl]-ethyl}-cyclohexyl)-3-(2-methoxy-phenyl)-urea |
| 20 | 505.49 | 5.807 | 95.59 | trans-1-(4-{2-[4-(2,3-Dichloro-phenyl)-piperazin-1-yl]-ethyl}-cyclohexyl)-3-(3-methoxy-phenyl)-urea |
| 21 | 439.43 | 4.816 | 96.25 | trans-1-Allyl-3-(4-{2-[4-(2,3-dichloro-phenyl)-piperazin-1-yl]-ethyl}-cyclohexyl)-urea |
| 22 | 535.52 | 5.901 | 99.52 | trans-1-(4-{2-[4-(2,3-Dichloro-phenyl)-piperazin-1-yl]-ethyl}-cyclohexyl)-3-(2,4-dimethoxy-phenyl)-urea |

| compound | mol weight | k' | Purity (HPLC Area %) | IUPAC |
|---|---|---|---|---|
| 23 | 519.52 | 6.092 | 98.37 | trans-1-(4-{2-[4-(2,3-Dichloro-phenyl)-piperazin-1-yl]-ethyl}-cyclohexyl)-3-(2-ethoxy-phenyl)-urea |
| 24 | 455.48 | 6.123 | 95.02 | trans-1-Butyl-3-(4-{2-[4-(2,3-dichloro-phenyl)-piperazin-1-yl]-ethyl}-cyclohexyl)-urea |
| 25 | 559.46 | 6.619 | 94.62 | trans-1-(4-{2-[4-(2,3-Dichloro-phenyl)-piperazin-1-yl]-ethyl}-cyclohexyl)-3-(4-trifluoromethoxy-phenyl)-urea |
| 26 | 533.59 | 6.324 | 99.43 | trans-1-Adamantan-1-yl-3-(4-{2-[4-(2,3-dichloro-phenyl)-piperazin-1-yl]-ethyl}-cyclohexyl)-urea |
| 27 | 521.56 | 5.976 | 88.03 | trans-1-(4-{2-[4-(2,3-Dichloro-phenyl)-piperazin-1-yl]-ethyl}-cyclohexyl)-3-(4-methylsulfanyl-phenyl)-urea |
| 28 | 551.56 | 6.441 | 85.42 | trans-1-Biphenyl-2-yl-3-(4-{2-[4-(2,3-dichloro-phenyl)-piperazin-1-yl]-ethyl}-cyclohexyl)-urea |
| 29 | 513.51 | 5.354 | 99.3 | trans-2-[3-(4-{2-[4-(2,3-Dichloro-phenyl)-piperazin-1-yl]-ethyl}-cyclohexyl)-ureido]-3-methyl-butyric acid methyl ester |
| 30 | 533.50 | 6.161 | 96.32 | trans-2-[3-(4-{2-[4-(2,3-Dichloro-phenyl)-piperazin-1-yl]-ethyl}-cyclohexyl)-ureido]-benzoic acid methyl ester |
| 31 | 500.48 | 5.704 | 93.41 | trans-1-(3-Cyano-phenyl)-3-(4-{2-[4-(2,3-dichloro-phenyl)-piperazin-1-yl]-ethyl}-cyclohexyl)-urea |
| 32 | 565.55 | 5.694 | 93.74 | trans-1-(4-{2-[4-(2,3-Dichloro-phenyl)-piperazin-1-yl]-ethyl}cyclohexyl)-3-(3,4,5-trimethoxy-phenyl)-urea |
| 33 | 481.51 | 5.591 | 99 | trans-1-Cyclohexyl-3-(4-{2-[4-(2,3-dichloro-phenyl)-piperazin-1-yl]-ethyl}-cyclohexyl)-urea |
| 34 | 441.45 | 5.121 | 96.93 | trans-1-(4-{2-[4-(2,3-Dichloro-phenyl)-piperazin-1-yl]-ethyl}-cyclohexyl)-3-propyl-urea |
| 35 | 491.53 | 5.689 | 98.53 | trans-1-(4-{2-[4-(2,3-Dichloro-phenyl)-piperazin-1-yl]-ethyl}-cyclohexyl)-3-phenyl-thiourea |
| 36 | 549.65 | 6.852 | 95.94 | trans-1-Adamantan-1-yl-3-(4-{2-[4-(2,3-dichloro-phenyl)-piperazin-1-yl]-ethyl}-cyclohexyl)-thiourea |
| 37 | 487.50 | 5.951 | 99 | trans-1-(4-{2-[4-(2,3-dichloro-phenyl)-piperazin-1-yl]-ethyl}-cyclohexyl)-3-ethoxycarbonyl-thiourea |
| 38 | 471.54 | 5.634 | 97.03 | trans-1-tert-Butyl-3-(4-{2-[4-(2,3-dichloro-phenyl)-piperazin-1-yl]-ethyl}-cyclohexyl)-thiourea |
| 39 | 505.56 | 5.909 | 99 | trans-1-Benzyl-3-(4-{2-[4-(2,3-dichloro-phenyl)-piperazin-1-yl]-ethyl}-cyclohexyl)-thiourea |
| 40 | 521.56 | 5.77 | 94.24 | trans-1-(4-{2-[4-(2,3-Dichloro-phenyl)-piperazin-1-yl]-ethyl}-cyclohexyl)-3-(2-methoxy-phenyl)-thiourea |
| 41 | 471.54 | 5.786 | 99 | trans-1-Butyl-3-(4-{2-[4-(2,3-dichloro-phenyl)-piperazin-1-yl]-ethyl}-cyclohexyl)-thiourea |
| 42 | 457.51 | 5.387 | 96.79 | trans-1-(4-{2-[4-(2,3-Dichloro-phenyl)-piperazin-1-yl]-ethyl}-cyclohexyl)-3-propyl-thiourea |
| 43 | 519.54 | 6.459 | 97.68 | trans-1-Benzoyl-3-(4-{2-[4-(2,3-dichloro-phenyl)-piperazin-1-yl]-ethyl}-cyclohexyl)-thiourea |
| 44 | 501.52 | 5.382 | 96.17 | trans-[3-(4-{2-[4-(2,3-Dichloro-phenyl)-piperazin-1-yl]-ethyl}-cyclohexyl)-thioureido]-acetic acid ethyl ester |
| 45 | 443.49 | 5.007 | 99 | trans-1-(4-{2-[4-(2,3-Dichloro-phenyl)-piperazin-1-yl]-ethyl}-cyclohexyl)-3-ethyl-thiourea |
| 46 | 541.59 | 6.401 | 96.26 | trans-1-(4-{2-[4-(2,3-Dichloro-phenyl)-piperazin-1-yl]-ethyl}-cyclohexyl)-3-naphthalen-1-yl-thiourea |
| 47 | 455.48 | 5.143 | 94.98 | trans-1-tert-Butyl-3-(4-{2-[4-(2,3-dichloro-phenyl)-piperazin-1-yl]-ethyl}-cyclohexyl)-urea |
| 48 | 475.47 | 5.481 | 95.69 | trans-1-(4-{2-[4-(2,3-Dichloro-phenyl)-piperazin-1-yl]-ethyl}-cyclohexyl)-urea |
| 49 | 489.49 | 5.491 | 94.42 | trans-1-Benzyl-3-(4-{2-[4-(2,3-dichloro-phenyl)-piperazin-1-yl]-ethyl}-cyclohexyl)-urea |
| 50 | 505.49 | 5.666 | 90.78 | trans-1-(4-{2-[4-(2,3-Dichloro-phenyl)-piperazin-1-yl]-ethyl}-cyclohexyl)-3-(4-methoxy-phenyl)-urea |
| 51 | 485.46 | 4.754 | 97.78 | trans-[3-(4-{2-[4-(2,3-Dichloro-phenyl)-piperazin-1-yl]-ethyl}-cyclohexyl)-ureido]-acetic acid ethyl ester |

The LC/MS analysis were performed using an HP 1100 binary gradient system, controlled by ChemStation software. HP diode array detector was used to acquire UV spectra at λ=210 nm. Analytical chromatographic experiments were made on Discovery $C_{16}$-Amide, 5 cm×4.6 mm×5 μm column with a flow rate of 0.8 ml/min for qualification (purity, capacity factor). All experiments were performed using HP MSD single quadruple mass spectrometer equipped with an electrospray ionisation source to determine the molecular mass.

$[k'=t_R-t_0/t_0$ $t_R$=retention time $t_0$=eluent retention time]

k'=capacity factor

The A eluent was water containing 0.1% TFA (Sigma, Germany), the B eluent was 95% acetonitrile (Merck, Germany) containing 0.1% TFA and 5% A eluent. Gradient elution was used, starting with 100% A eluent and processing to 100% B eluent over a periode of 15 minutes.

Pharmaceutical Formulations

| a) Intravenous injection | |
|---|---|
| Compound of formula (I) | 1-40 mg |
| Buffer | to pH ca 7 |
| Solvent/complexing agent | to 100 ml |
| b) Bolus injection | |
| Compound of formula (I) | 1-40 mg |
| Buffer | to pH ca 7 |
| Co-solvent | to 5 ml |

Buffer: suitable buffers include citrate, phosphate, sodium hydroxide/hydrochloric acid.

Solvent: typically water but may also include cyclodextrins (1-100 mg) and co-solvents, such as propylene glycol, polyethylene glycol and alcohol.

c) Tablet

| | |
|---|---|
| Compound of formula (I) | 1-40 mg |
| Diluent/Filter(may also include cyclodextrins) | 50-250 mg |
| Binder | 5-25 mg |
| Disintegrant (may also include cyclodextrins) | 5-50 mg |
| Lubricant | 1-5 mg |
| Cyclodextrin | 1-100 mg |

Diluent: e.g. mycrocrystalline cellulose, lactose starch.
Binder: e.g. polyvinylpyrrolidone, hydroxypropylmethylcellulose.
Disintegrant: e.g. sodium starch glycolate, crospovidone.
Lubricant: e.g. magnesium stearate, sodium stearyl fumarate d) Oral Suspension

| | |
|---|---|
| Compound of formula (I) | 1-40 mg |
| Suspending agent | 0.1-10 mg |
| Diluent | 20-60 mg |
| Preservative | 0.01-1.0 mg |
| Buffer | to pH ca 5-8 |
| Co-solvent | 0-40 mg |
| Flavour | 0.01-1.0 mg |
| Colourant | 0.001-0.1 mg |

Suspending agent: e.g. xanthan gum, mycrocrystalline cellulose.
Diluent: e.g. sorbitol solution, typically water.
Preservative: e.g. sodium benzoate.
Buffer: e.g. citrate.
Co-solvent: e.g. alcohol, propylene glycol, polyethylene glycol, cyclodextrin.

What we claim:

1. A compound of formula (I):

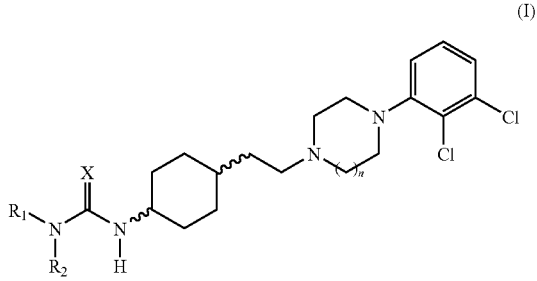

(I)

wherein
R$_1$ and R$_2$ represent independently a substituent selected from hydrogen, alkyl, alkenyl, aryl, cycloalkyl, or aroyl, or R$_1$ and R$_2$ together with the adjacent nitrogen atom form a heterocyclic ring;
X represents an oxygen or sulphur atom; and
n is 1,
and/or geometric isomers and/or stereoisomers and/or diastereomers and/or salts thereof.

2. A compound of claim 1, wherein
R$_1$ and R$_2$ represent independently hydrogen, or
a straight or branched C$_{1-6}$ alkyl optionally substituted with one or more C$_{1-6}$ alkoxycarbonyl, aryl, or (C$_{1-6}$ alkoxycarbonyl)-C$_{1-6}$ alkyl group, or R$_1$ and R$_2$ together with the adjacent nitrogen atom form a heterocyclic ring, which is a saturated or unsaturated optionally substituted monocyclic or bicyclic ring, which may contain further heteroatoms selected from O, N, or S, or C$_{2-7}$ alkenyl with 1 to 3 double bonds, or
a mono-, bi- or tricyclic aryl optionally substituted with one or more C$_{1-6}$ alkoxy, trifluoro C$_{1-6}$ alkoxy, C$_{1-6}$ alkoxycarbonyl, C$_{1-6}$ alkanoyl, aryl, C$_{1-6}$ alkylthio, halogen or cyano, or an optionally substituted mono-, bi- or tricyclic cycloalkyl group, or aroyl group.

3. A compound of claim 2, wherein
R$_1$ and R$_2$ represent independently
(i) hydrogen,
(ii) a straight or branched C$_{1-6}$ alkyl optionally substituted with one or more alkoxycarbonyl, phenyl or (C$_{1-6}$ alkoxycarbonyl)-C$_{1-6}$ alkyl group,
(iii) R$_1$ and R$_2$ together with the adjacent nitrogen atom form a hetero-monocyclic ring, which may be optionally substituted by C$_{1-6}$ alkyl or hydroxyl and which may contain further heteroatoms selected from O or N,
(iv) C$_{2-7}$ alkenyl with 1 double bond,
(v) phenyl or naphthyl group optionally substituted with one or more C$_{1-6}$ alkoxy, trifluoro-C$_{1-6}$ alkoxy, C$_{1-6}$ alkoxycarbonyl, C$_{1-6}$ alkanoyl, aryl, C$_{1-6}$ alkylthio, halogen or cyano,
(vi) cyclohexyl or adamantyl group, or
(vii) benzoyl group.

4. A compound of claim 3,
wherein R$_1$ and R$_2$ represent independently
hydrogen, a straight or branched C$_{1-6}$ alkyl optionally substituted with C$_{1-6}$ alkoxycarbonyl, or phenyl or R$_1$ and R$_2$ together with the adjacent nitrogen atom form a pyrrolidine, piperazine, piperidine or morpholine ring, which is optionally substituted by C$_{1-6}$ alkyl or a hydroxy group, allyl, phenyl optionally substituted with one or more C$_{1-6}$ alkoxy, cyano or C$_{1-6}$ alkanoyl, or cyclohexyl;
X represents oxygen or sulphur; and n is 1.

5. A compound selected from
trans-1-{4-[2-[4-(2,3-dichlorophenyl)-piperazin-1-yl]-ethyl]-cyclohexyl}-3-methyl-urea,
trans-1-{4-[2-[4-(2,3-dichlorophenyl)-piperazin-1-yl]-ethyl]-cyclohexyl}-3-propyl-urea,
trans-1-{4-[2-[4-(2,3-dichlorophenyl)-piperazin-1-yl]-ethyl]-cyclohexyl}-3-isopropyl-urea,
trans-N-{4-[2-[4-(2,3-dichlorophenyl)-piperazin-1-yl]-ethyl]-cyclohexyl}-pyrrolidine-1-carboxamide,
trans-1-{4-[2-[4-(2,3-dichlorophenyl)-piperazin-1-yl]-ethyl]-cyclohexyl}-3,3-diethyl-urea;
trans-1-{4-[2-[4-(2,3-dichlorophenyl)-piperazin-1-yl]-ethyl]-cyclohexyl}-3-ethyl-3-methyl-urea;
trans-1-{4-[2-[4-(2,3-dichlorophenyl)-piperazin-1-yl]-ethyl]-cyclohexyl}-3-methyl-3-propyl-urea;
trans-1-{4-[2-[4-(2,3-dichlorophenyl)-piperazin-1-yl]-ethyl]-cyclohexyl}-urea;
trans-N-{4-[2-[4-(2,3-dichlorophenyl)-piperazin-1-yl]-ethyl]-cyclohexyl}-piperazine-1-carboxamide;
trans-N-{4-[2-[4-(2,3-dichlorophenyl)-piperazin-1-yl]-ethyl]-cyclohexyl}-4-methyl-piperazine-1-carboxamide;
trans-N-{4-[2-[4-(2,3-dichlorophenyl)-piperazin-1-yl]-ethyl]-cyclohexyl}-morpholine-4-carboxamide;

trans-N-{4-[2-[4-(2,3-dichlorophenyl)-piperazin-1-yl]-ethyl]-cyclohexyl}-piperidine-1-carboxamide;
trans-N-{4-[2-[4-(2,3-dichlorophenyl)-piperazin-1-yl]-ethyl]-cyclohexyl}-4-hydroxy-piperidine-1-carboxamide;
trans-1-{4-[2-[4-(2,3-dichlorophenyl)-piperazin-1-yl]-ethyl]-cyclohexyl}-3,3-dimethyl-urea,
trans-1-{4-[2-[4-(2,3-dichlorophenyl)-piperazin-1-yl]-ethyl]-cyclohexyl}-3-ethyl-urea,
trans-1-(4-{2-[4-(2,3-dichloro-phenyl)-piperazin-1-yl]-ethyl}-cyclohexyl)-3-(2-methoxy-phenyl)-urea,
trans-1-(4-{2-[4-(2,3-dichloro-phenyl)-piperazin-1-yl]-ethyl}-cyclohexyl)-3-(3-methoxy-phenyl)-urea,
trans-1-allyl-3-(4-{2-[4-(2,3-dichloro-phenyl)-piperazin-1-yl]-ethyl}-cyclohexyl)-urea,
trans-1-(4-{2-[4-(2,3-dichloro-phenyl)-piperazin-1-yl]-ethyl}-cyclohexyl)-3-(2,4-dimethoxy-phenyl)-urea,
trans-1-(4-{2-[4-(2,3-dichloro-phenyl)-piperazin-1-yl]-ethyl}-cyclohexyl)-3-(2-ethoxy-phenyl)-urea,
trans-1-butyl-3-(4-{2-[4-(2,3-dichloro-phenyl)-piperazin-1-yl]-ethyl}-cyclohexyl)-urea,
trans-1-(4-{2-[4-(2,3-dichloro-phenyl)-piperazin-1-yl]-ethyl}-cyclohexyl)-3-(4-trifluoromethoxy-phenyl)-urea,
trans-1-adamantan-1-yl-3-(4-{2-[4-(2,3-dichloro-phenyl)-piperazin-1-yl]-ethyl}-cyclohexyl)-urea,
trans-1-(4-{2-[4-(2,3-dichloro-phenyl)-piperazin-1-yl]-ethyl}-cyclohexyl)-3-(4-methylsulfanyl-phenyl)-urea,
trans-1-biphenyl-2-yl-3-(4-{2-[4-(2,3-dichloro-phenyl)-piperazin-1-yl]-ethyl}-cyclohexyl)-urea
trans-2-[3-(4-{2-[4-(2,3-dichloro-phenyl)-piperazin-1-yl]-ethyl}-cyclohexyl)-ureido]-3-methyl-butyric acid methyl ester,
trans-2-[3-(4-{2-[4-(2,3-dichloro-phenyl)-piperazin-1-yl]-ethyl}-cyclohexyl)-ureido]-benzoic acid methyl ester,
trans-1-(3-cyano-phenyl)-3-(4-{2-[4-(2,3-dichloro-phenyl)-piperazin-1-yl]-ethyl}-cyclohexyl)-urea,
trans-1-(4-{2-[4-(2,3-dichloro-phenyl)-piperazin-1-yl]-ethyl}cyclohexyl)-3-(3,4,5-trimethoxy-phenyl)-urea,
trans-1-cyclohexyl-3-(4-{2-[4-(2,3-dichloro-phenyl)-piperazin-1-yl]-ethyl}-cyclohexyl)-urea,
trans-1-(4-{2-[4-(2,3-dichloro-phenyl)-piperazin-1-yl]-ethyl}-cyclohexyl)-3-phenyl-thiourea,
trans-1-adamantan-1-yl-3-(4-{2-[4-(2,3-dichloro-phenyl)-piperazin-1-yl]-ethyl}-cyclohexyl)-thiourea,
trans-1-(4-{2-[4-(2,3-dichloro-phenyl)-piperazin-1-yl]-ethyl}-cyclohexyl)-3-ethoxycarbonyl-thiourea,
trans-1-tert-butyl-3-(4-{2-[4-(2,3-dichloro-phenyl)-piperazin-1-yl]-ethyl}-cyclohexyl)-thiourea,
trans-1-benzyl-3-(4-{2-[4-(2,3-dichloro-phenyl)-piperazin-1-yl]-ethyl}-cyclohexyl)-thiourea,
trans-1-(4-{2-[4-(2,3-dichloro-phenyl)-piperazin-1-yl]-ethyl}-cyclohexyl)-3-(2-methoxy-phenyl)-thiourea,
trans-1-butyl-3-(4-{2-[4-(2,3-dichloro-phenyl)-piperazin-1-yl]-ethyl}-cyclohexyl)-thiourea,
trans-1-(4-{2-[4-(2,3-dichloro-phenyl)-piperazin-1-yl]-ethyl}-cyclohexyl)-3-propyl-thiourea,
trans-1-benzoyl-3-(4-{2-[4-(2,3-dichloro-phenyl)-piperazin-1-yl]-ethyl}-cyclohexyl)-thiourea,
trans-[3-(4-{2-[4-(2,3-dichloro-phenyl)-piperazin-1-yl]-ethyl}-cyclohexyl)-thioureido]-acetic acid ethyl ester,
trans-1-(4-{2-[4-(2,3-dichloro-phenyl)-piperazin-1-yl]-ethyl}-cyclohexyl)-3-ethyl-thiourea,
trans-1-(4-{2-[4-(2,3-dichloro-phenyl)-piperazin-1-yl]-ethyl}-cyclohexyl)-3-naphthalen-1-yl-thiourea,
trans-1-tert-butyl-3-(4-{2-[4-(2,3-dichloro-phenyl)-piperazin-1-yl]-ethyl}-cyclohexyl)-urea,
trans-1-(4-{2-[4-(2,3-dichloro-phenyl)-piperazin-1-yl]-ethyl}-cyclohexyl)-3-phenyl-urea,
trans-1-benzyl-3-(4-{2-[4-(2,3-dichloro-phenyl)-piperazin-1-yl]-ethyl}-cyclohexyl)-urea,
trans-1-(4-{2-[4-(2,3-dichloro-phenyl)-piperazin-1-yl]-ethyl}-cyclohexyl)-3-(4-methoxy-phenyl)-urea,
trans-[3-(4-{2-[4-(2,3-dichloro-phenyl)-piperazin-1-yl]-ethyl}-cyclohexyl)-ureido]-acetic acid ethyl ester,
and/or geometric isomers and/or stereoisomers and/or diastereomers and/or salts thereof.

6. A process for preparing a compound of formula (I):

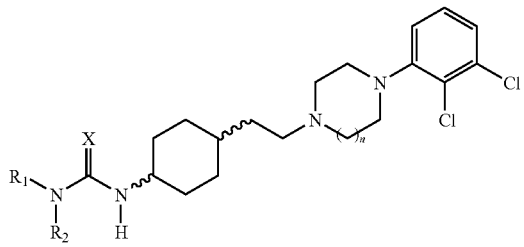

wherein
$R_1$ and $R_2$ represent independently a substituent selected from hydrogen, alkyl, alkenyl, aryl, cycloalkyl, aroyl, or $R_1$ and $R_2$ together with the adjacent nitrogen atom form a heterocyclic ring;
X represents an oxygen or sulphur atom; and
n is 1,
and/or geometric isomers and/or stereoisomers and/or diastereomers and/or salts thereof, which comprises:
a) forming an amide bond between a (thio)carbamoyl-chloride of formula (II):

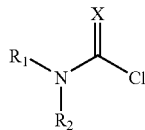

wherein $R_1$, $R_2$ and X are as defined above for formula (I), and an amine of formula (III):

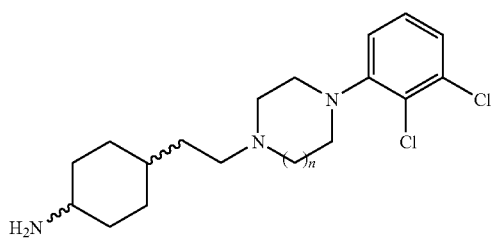

wherein n is as defined above for formula (I), or
b) forming an amide bond between the iso(thio)cyanate of formula (IV):

$$R_1-N=C=X \quad (IV)$$

wherein $R_1$ and X are as defined above for the formula (I), and an amine of formula (III):

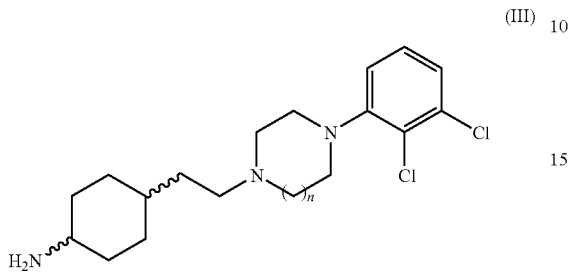

(III)

wherein n is as defined above for the formula (I),
or
c) transforming in situ an amine of formula (III) to an iso(thio)cyanate and reacting the latter with an amine of formula (V):

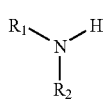

(V)

wherein $R_1$ and $R_2$ are as described above for the formula (I),
and
interconverting one compound (I) obtained by any of method a) to c), wherein $R_1$, $R_2$, X and n are as defined for compound (I) to a different compound of formula (I) wherein $R_1$, $R_2$, X and n are as defined for compound (I);
where appropriate, separating the enantiomers and/or diastereomers, and/or cis- and/or trans-isomers of compounds of formula (I), or intermediates thereto wherein $R_1$, $R_2$, X and n are as defined for compound (I) by conventional methods;
and optionally thereafter forming salts.

7. The process of claim 6, wherein
$R_1$ and $R_2$ represent independently
hydrogen, or
a straight or branched $C_{1-6}$ alkyl optionally substituted with one or more $C_{1-6}$ alkoxycarbonyl, aryl, or ($C_{1-6}$ alkoxycarbonyl)-$C_{1-6}$ alkyl group, or $R_1$ and $R_2$ together with the adjacent nitrogen atom form a heterocyclic ring, which is a saturated or unsaturated optionally substituted monocyclic or bicyclic ring, which may contain further heteroatoms selected from O, N, or S, or $C_{2-7}$ alkenyl with 1 to 3 double bond, or
a mono-, bi- or tricyclic aryl optionally substituted with one or more $C_{1-6}$ alkoxy, trifluoro $C_{1-6}$ alkoxy, $C_{1-6}$ alkoxycarbonyl, $C_{1-6}$ alkanoyl, aryl, $C_{1-6}$ alkylthio, halogen or cyano, or
an optionally substituted mono-, bi- or tricyclic cycloalkyl group, or aroyl group.

8. The process of claim 7, wherein
$R_1$ and $R_2$ represent independently
hydrogen, or a straight or branched $C_{1-6}$ alkyl optionally substituted with one or more alkoxycarbonyl, phenyl or ($C_{1-6}$ alkoxycarbonyl)-$C_{1-6}$ alkyl group or $R_1$ and $R_2$ may form a heterocyclic ring with the adjacent nitrogen atom, which may be optionally substituted by $C_{1-6}$ alkyl or hydroxy substituted monocyclic ring, which may contain further heteroatoms selected from O or N, or
$C_{2-7}$ alkenyl with 1 double bond, or
phenyl or naphthyl group optionally substituted with one or more $C_{1-6}$ alkoxy, trifluoro-$C_{1-6}$ alkoxy, $C_{1-6}$ alkoxycarbonyl, $C_{1-6}$ alkanoyl, aryl, $C_{1-6}$ alkylthio, halogen or cyano, or cyclohexyl or adamantyl group, or benzoyl group.

9. The process of claim 8, wherein
$R_1$ and $R_2$ represent independently
(i) hydrogen,
(ii) a straight or branched $C_{1-6}$ alkyl optionally substituted with $C_{1-6}$ alkoxycarbonyl,
(iii) $R_1$ and $R_2$ form with the adjacent nitrogen atom a pyrrolidine, piperazine, piperidine or morpholine ring optionally substituted by $C_{1-6}$ alkyl or hydroxy,
(iv) allyl,
(v) phenyl optionally substituted with one or more $C_{1-6}$ alkoxy, cyano or alkanoyl, or
(vi) cyclohexyl;
X represents oxygen or sulphur; and
n is 1.

10. A pharmaceutical composition comprising a compound of formula (I):

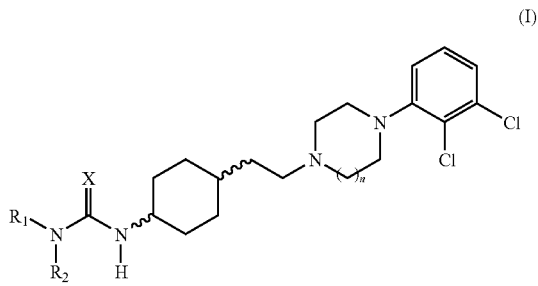

(I)

wherein
$R_1$ and $R_2$ represent independently a substituent selected from hydrogen, alkyl, alkenyl, aryl, cycloalkyl, or aroyl, or $R_1$ and $R_2$ together with the adjacent nitrogen atom form a heterocyclic ring;
X represents an oxygen or sulphur atom; and
n is 1,
and/or geometric isomers and/or stereoisomers and/or diastereomers and/or physiologically acceptable salts thereof and one or more physiologically acceptable carriers therefore.

11. The pharmaceutical composition of claim 10, wherein
$R_1$ and $R_2$ represent independently
hydrogen, or
a straight or branched $C_{1-6}$ alkyl optionally substituted with one or more alkoxycarbonyl, aryl, or ($C_{1-6}$ alkoxycarbonyl)-$C_{1-6}$ alkyl group, or $R_1$ and $R_2$ together with the adjacent nitrogen atom form a heterocyclic ring, which is a saturated or unsaturated optionally substituted monocyclic or bicyclic ring, which may contain further heteroatoms selected from O, N, or S, or C$_{2-7}$ alkenyl with 1 to 3 double bond, or a mono-, bi- or tricyclic aryl optionally substituted with one or more C$_{1-6}$ alkoxy, trifluoro-C$_{1-6}$ alkoxy, C$_{1-6}$ alkoxycarbonyl, C$_{1-6}$ alkanoyl, aryl, C$_{1-6}$ alkylthio, halogen or cyano, or an optionally substituted mono-, bi- or tricyclic cycloalkyl group, or aroyl group.

12. The pharmaceutical composition of claim 11, wherein R$_1$ and R$_2$ represent independently (i) hydrogen, (ii) a straight or branched C$_{1-6}$ alkyl optionally substituted with one or more C$_{1-6}$ alkoxycarbonyl, phenyl or (C$_{1-6}$ alkoxycarbonyl)-C$_{1-6}$ alkyl group (iii) R$_1$ and R$_2$ together with the adjacent nitrogen atom form a hetero-monocyclic ring, which may be optionally substituted by C$_{1-6}$ alkyl or hydroxyl and which may contain further heteroatoms selected from O or N, or C$_{2-7}$ alkenyl with 1 double bond, (iv) a phenyl or naphthyl group optionally substituted with one or more C$_{1-6}$ alkoxy, trifluoro-C$_{1-6}$ alkoxy, C$_{1-6}$ alkoxycarbonyl, C$_{1-6}$ alkanoyl, aryl, C$_{1-6}$ alkylthio, halogen or cyano, or (v) a cyclohexyl or adamantyl group, or (vi) a benzoyl group.

13. The pharmaceutical composition of claim 12, wherein R$_1$ and R$_2$ represent independently hydrogen, a straight or branched C$_{1-6}$ alkyl optionally substituted with C$_{1-6}$ alkoxycarbonyl, or phenyl or R$_1$ and R$_2$ together with the adjacent nitrogen atom form a pyrrolidine, piperazine, piperidine or morpholine ring, which is optionally substituted by C$_{1-6}$ alkyl or a hydroxy group, allyl, phenyl optionally substituted with one or more C$_{1-6}$ alkoxy, cyano or C$_{1-6}$ alkanoyl, or cyclohexyl;

X represents oxygen or sulphur; and n is 1.

14. A method of treating a condition which requires modulation of dopamine receptor(s) which comprises administering to a subject in need thereof an effective amount of a compound of formula (I)

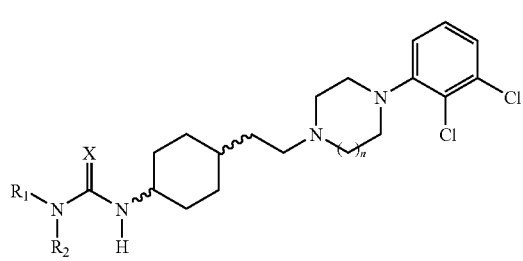

(I)

wherein

R$_1$ and R$_2$ represent independently a substituent selected from hydrogen, alkyl, alkenyl, aryl, cycloalkyl, aroyl, or R$_1$ and R$_2$ together with the adjacent nitrogen atom form a heterocyclic ring;

X represents an oxygen or sulphur atom; and n is 1, and/or geometric isomers and/or stereoisomers and/or diastereomers and/or physiologically acceptable salts thereof; and the condition which requires modulation of dopamine receptor(s) is selected from the group consisting of: psychosis, cognitive impairment accompanying schizophrenia, mild-to-moderate cognitive deficits, dementia, psychotic states associated with dementia, psychotic depression, mania, paranoid and delusional disorders, dyskinetic disorders, neuroleptics-induced parkinsonism, tardive dyskinesia, eating disorders, attention deficit disorder, hyperactivity disorders in children, depression, anxiety, sexual dysfunction, sleep disorders, emesis, aggression, autism, and drug abuse.

15. The method of claim 14, wherein R$_1$ and R$_2$ represent independently hydrogen, or a straight or branched C$_{1-6}$ alkyl optionally substituted with one or more alkoxycarbonyl, aryl, or (C$_{1-6}$ alkoxycarbonyl)-C$_{1-6}$ alkyl group, or R$_1$ and R$_2$ together with the adjacent nitrogen atom form a heterocyclic ring, which is a saturated or unsaturated optionally substituted monocyclic or bicyclic ring, which may contain further heteroatoms selected from O, N, or S, or C$_{2-7}$ alkenyl with 1 to 3 double bond, or a mono-, bi- or tricyclic aryl optionally substituted with one or more C$_{1-6}$ alkoxy, trifluoro C$_{1-6}$ alkoxy, C$_{1-6}$ alkoxycarbonyl, C$_{1-6}$ alkanoyl, aryl, C$_{1-6}$ alkylthio, halogen or cyano, or an optionally substituted mono-, bi- or tricyclic cycloalkyl group, or aroyl group.

16. The method of claim 15, wherein R$_1$ and R$_2$ represent independently (i) hydrogen, (ii) a straight or branched C$_{1-6}$ alkyl optionally substituted with one or more C$_{1-6}$ alkoxycarbonyl, phenyl or (C$_{1-6}$ alkoxycarbonyl)-C$_{1-6}$ alkyl group, (iii) R$_1$ and R$_2$ together with the adjacent nitrogen atom form a hetero-monocyclic ring, which may be optionally substituted by C$_{1-6}$ alkyl or hydroxyl and which may contain further heteroatoms selected from O or N, (iv) C$_{2-7}$ alkenyl with 1 double bond, (v) phenyl or naphthyl group optionally substituted with one or more C$_{1-6}$ alkoxy, trifluoro-C$_{1-6}$ alkoxy, C$_{1-6}$ alkoxycarbonyl, C$_{1-6}$ alkanoyl, aryl, C$_{1-6}$ alkylthio, halogen or cyano, (vi) cyclohexyl or adamantyl group, or (vii) benzoyl group.

17. The method of claim 16, wherein R$_1$ and R$_2$ represent independently hydrogen, or a straight or branched C$_{1-6}$ alkyl optionally substituted with C$_{1-6}$ alkoxycarbonyl, or phenyl or R$_1$ and R$_2$ together with the adjacent nitrogen atom form a pyrrolidine, piperazine, piperidine or morpholine ring, which is optionally substituted by C$_{1-6}$ alkyl or a hydroxy group, allyl, phenyl optionally substituted with one or more C$_{1-6}$ alkoxy, cyano or C$_{1-6}$ alkanoyl, or cyclohexyl, X represents oxygen or sulphur, and n is 1.

18. The method of any of claims 14 to 17, wherein the dopamine receptor is a dopamine D$_3$ and/or D$_2$ receptor.

19. A compound having the formula:

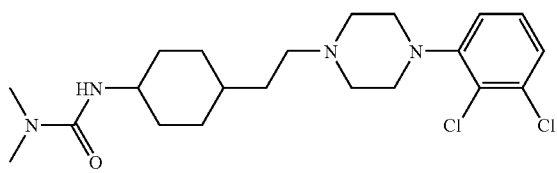

or a salt thereof.

20. A pharmaceutical composition comprising the compound of claim 19 and a physiologically acceptable carrier.

21. A method for treating a condition in a patient comprising administering to the patient the pharmaceutical composition of claim 20, wherein the condition is selected from the group consisting of: psychosis, cognitive impairment accompanying schizophrenia, mild-to-moderate cognitive deficits, dementia, psychotic states associated with dementia, psychotic depression, mania, paranoid and delusional disorders, dyskinetic disorders, neuroleptics-induced parkinsonism, tardive dyskinesia, eating disorders, attention deficit disorder, hyperactivity disorders in children, depression, anxiety, sexual dysfunction, sleep disorders, emesis, aggression, autism, and drug abuse.

22. A method for treating schizophrenia comprising administering to a patient with schizophrenia the pharmaceutical composition of claim 20.

23. A method for treating mania comprising administering to a patient with mania the pharmaceutical composition of claim 20.

24. A compound having the formula:

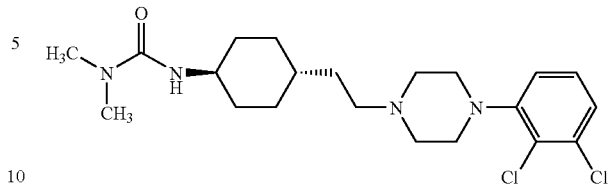

or a salt thereof.

25. A pharmaceutical composition comprising the compound of claim 24 and a physiologically acceptable carrier.

26. A method for treating a condition in a patient comprising administering to the patient the pharmaceutical composition of claim 24, wherein the condition is selected from the group consisting of: psychosis, cognitive impairment accompanying schizophrenia, mild-to-moderate cognitive deficits, dementia, psychotic states associated with dementia, psychotic depression, mania, paranoid and delusional disorders, dyskinetic disorders, neuroleptics-induced parkinsonism, tardive dyskinesia, eating disorders, attention deficit disorder, hyperactivity disorders in children, depression, anxiety, sexual dysfunction, sleep disorders, emesis, aggression, autism, and drug abuse.

27. A method for treating schizophrenia comprising administering to a patient with schizophrenia the pharmaceutical composition of claim 24.

28. A method for treating mania comprising administering to a patient with mania the pharmaceutical composition of claim 24.

* * * * *

UNITED STATES PATENT AND TRADEMARK OFFICE
CERTIFICATE OF CORRECTION

PATENT NO. : 7,737,142 B2
APPLICATION NO. : 11/337275
DATED : June 15, 2010
INVENTOR(S) : Eva Againe Csongor It is certified that error appears in the above-identified patent and that said Letters Patent is hereby corrected as shown below:

Column 1
Line 1, change "(THIO) CARBAMOYL-CYCLOHEXANE" to
-- (THIO)CARBAMOYL-CYCLOHEXANE --

Column 2
Line 12, change "Relvance" to -- Relevance --

Column 18
Line 20, change "one or more" to -- one or more $C_{1-6}$ --

Column 19
Line 30, after "urea" insert -- , --

Column 22
Line 2, change "one or more" to -- one or more $C_{1-6}$ --

Line 25, change "or" to -- or $C_{1-6}$ --

Line 61, change "one or more" to -- one or more $C_{1-6}$ --

Column 23
Line 48, after "(I)" insert -- : --

Column 24
Line 21, change "one or more" to -- one or more $C_{1-6}$ --

Signed and Sealed this

Nineteenth Day of October, 2010

David J. Kappos
*Director of the United States Patent and Trademark Office*

UNITED STATES PATENT AND TRADEMARK OFFICE
CERTIFICATE OF CORRECTION

PATENT NO. : 7,737,142 B2  Page 1 of 1
APPLICATION NO. : 11/337275
DATED : June 15, 2010
INVENTOR(S) : Eva Againe Csongor It is certified that error appears in the above-identified patent and that said Letters Patent is hereby corrected as shown below:

Title Page, Item (54) and at Column 1, line 1, in the title change "(THIO) CARBAMOYL-CYCLOHEXANE" to -- (THIO)CARBAMOYL-CYCLOHEXANE --

Column 2
Line 12, change "Relvance" to -- Relevance --

Column 18
Line 20, change "one or more" to -- one or more $C_{1-6}$ --

Column 19
Line 30, after "urea" insert -- , --

Column 22
Line 2, change "one or more" to -- one or more $C_{1-6}$ --

Line 25, change "or" to -- or $C_{1-6}$ --

Line 61, change "one or more" to -- one or more $C_{1-6}$ --

Column 23
Line 48, after "(I)" insert -- : --

Column 24
Line 21, change "one or more" to -- one or more $C_{1-6}$ --

This certificate supersedes the Certificate of Correction issued October 19, 2010.

Signed and Sealed this

Twenty-third Day of November, 2010

David J. Kappos
*Director of the United States Patent and Trademark Office*